(12) United States Patent
Lavery

(10) Patent No.: US 6,594,607 B2
(45) Date of Patent: Jul. 15, 2003

(54) MEDICAL SCREENING APPARATUS AND METHOD

(76) Inventor: Kevin T. Lavery, 4521 Sid Dr., Jackson, MI (US) 49201

( * ) Notice: Subject to any disclaimer, the term of this patent is extended or adjusted under 35 U.S.C. 154(b) by 98 days.

(21) Appl. No.: 09/783,449

(22) Filed: Feb. 14, 2001

(65) Prior Publication Data

US 2001/0025226 A1 Sep. 27, 2001

Related U.S. Application Data

(60) Provisional application No. 60/183,592, filed on Feb. 18, 2000.

(51) Int. Cl.$^7$ ................................................ A61B 3/00
(52) U.S. Cl. .................... 702/108; 600/437; 600/400
(58) Field of Search .................... 702/108; 600/437, 600/400; 128/904, 858, 859, 845, 200.28, 201.12; 345/733; 351/210, 206, 246

(56) References Cited

U.S. PATENT DOCUMENTS

| | | | | |
|---|---|---|---|---|
| 5,094,521 A | * | 3/1992 | Jolson et al. | 351/206 |
| 5,655,084 A | * | 8/1997 | Pinsky et al. | 705/3 |
| 5,715,823 A | * | 2/1998 | Wood et al. | 128/904 |
| 5,897,498 A | * | 4/1999 | Canfield et al. | 600/437 |
| 6,353,445 B1 | * | 3/2002 | Babula et al. | 345/733 |

* cited by examiner

*Primary Examiner*—Bryan Bui
*Assistant Examiner*—Hien Vo
(74) *Attorney, Agent, or Firm*—Young & Basile, PC

(57) ABSTRACT

A medical screening apparatus and method includes a housing containing a user interface, an automatic medical test apparatus and a transmitting means for communicating the output of the medical test apparatus to a remote site for analysis. In one aspect, the user interface is a video display terminal capable of receiving user data and for displaying the medical test output. Preferably, the test output is automatically transmitted via a global telecommunication network, such as the Internet, to the remote site.

18 Claims, 2 Drawing Sheets

MEDICAL SCREENING APPARATUS AND METHOD

CROSS REFERENCE TO CO-PENDING APPLICATION

This application claims the benefit of the filing date of co-pending Provisional Patent Application Ser. No. 60/183,592 filed Feb. 18, 2000, and entitled Retinal Screening Apparatus.

BACKGROUND

Diabetes is a leading cause of blindness in the United States. Unfortunately, despite access to medical care, many patients are going undiagnosed in terms of their diabetic eye disease. Many efforts have been directed to screening; however, such efforts are still ineffective. An HMO states that only 33% of its diabetic patients are actually obtaining yearly eye exams, despite widespread educational efforts. Glaucoma is another serious cause of blindness in the United States that is under detected.

In an effort to increase the percentage of patients who are obtaining yearly eye exams to detect diabetes effects, glaucoma and other eye problems in an earliest possible stage, a new approach is warranted.

SUMMARY

The present invention is an apparatus and method for conducting a medical screening test on a user patient.

In one aspect of the invention, the medical screening apparatus includes a housing, a user interface mounted in the housing for inputting patient-related data, medical test apparatus mounted in the housing for conducting a medical test on a user and generating a test output, and means for communicating with the medical test apparatus for transmitting the test output and patient data to a remote site for analysis.

In one aspect, the apparatus further includes a control means in the housing for controlling the user interface, activation of the medical test apparatus and operation of the transmitting means. Preferably the control means includes a central processing unit executing a control program stored in a memory coupled to the central processing unit.

The transmitting means preferably comprises means for communicating the test output to the remote site via a global telecommunication network, such as the Internet.

In another aspect, the user interface preferably comprises a video display terminal. The display terminal can be capable of receiving only user input data in response to visual prompts generated by the control means. Alternately, the video display terminal is also capable of displaying the test output.

In one specific aspect, the medical test apparatus is a retinal screening apparatus. The retinal screening apparatus preferably includes a digital retinal camera. Means are provided for establishing a predetermined position of the user's or patient's eye with respect to the camera. This position may be provided by a chin support mounted at a fixed distance from the camera in the housing or a seat mounted on the housing at a fixed distance from the camera.

In another aspect, the invention is a method of automatically conducting a medical screening test on a user or patient. The method includes steps of providing a housing, providing a user interface in the housing for receiving user-related data, providing a medical test apparatus in the housing for automatically executing a medical test on a user and generating a test output, and transmitting the test output to a remote site for analysis.

Preferably, the user interface is implemented by providing a video display terminal in the housing which is capable of receiving user data in response to visual prompts generated by a control means on the video display terminal and/or displaying the medical test output on the display terminal.

The method further includes the step of providing the test apparatus as a retinal screening apparatus which includes a digital retinal camera. The method includes the steps of establishing a predetermined position of the patient's eye from the digital camera for implementing the retinal screening test.

The medical screening apparatus and method of the present invention affords numerous advantages. The primary advantage is the easy and quick taking of a medical screening test on a user or patient. This simple procedure causes users to more readily have the medical screening test performed so as to detect any diseases at an earlier stage. The entire operation of the apparatus is automated so as to simplify its use by numerous users when the apparatus is placed in a public location, such as a shopping mall, etc.

The apparatus is also capable of taking one or more tests. The use of the global telecommunication network for transmitting the test results enables each test to be analyzed by a central test organization for test result consistency.

BRIEF DESCRIPTION OF THE DRAWING

The various features, advantages and other uses of the present invention will become more apparent by referring to the following detail description and drawing in which.

DESCRIPTION OF THE PREFERRED EMBODIMENTS

Figure 1:
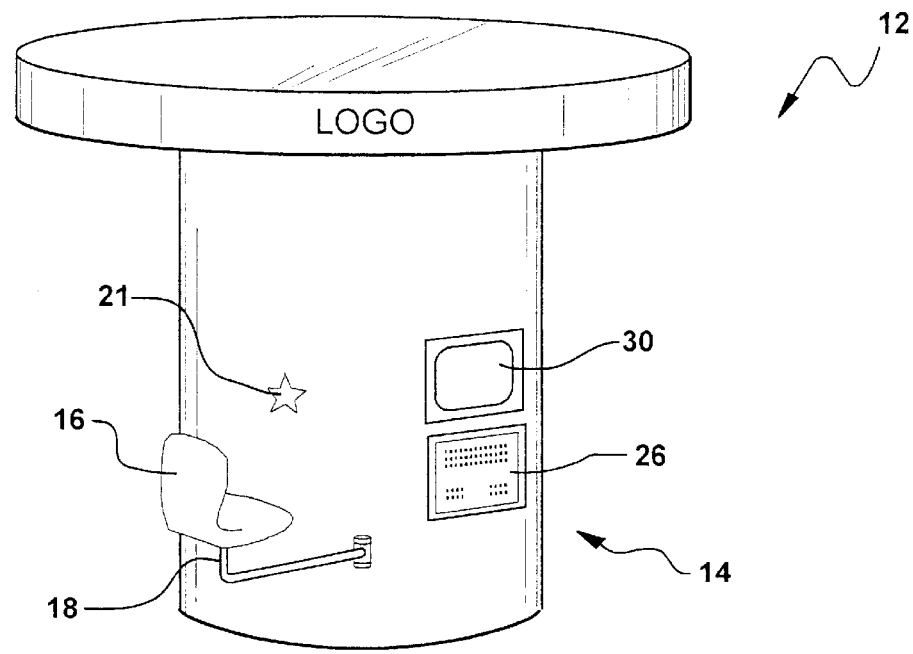
FIG. 1 is a pictorial representation of a kiosk type remote unit used in the retinal screening apparatus of the present invention.

Referring now to the drawing, and to FIGS. 1–4 in particular, there is depicted a retinal screening apparatus and system according to the present invention. The system 10, shown in FIG. 4, includes at least one and preferably a plurality of remote units 12 which are each situated in a public place capable of exposure to large numbers of people, such as malls, movie theaters, etc.

Figure 2:
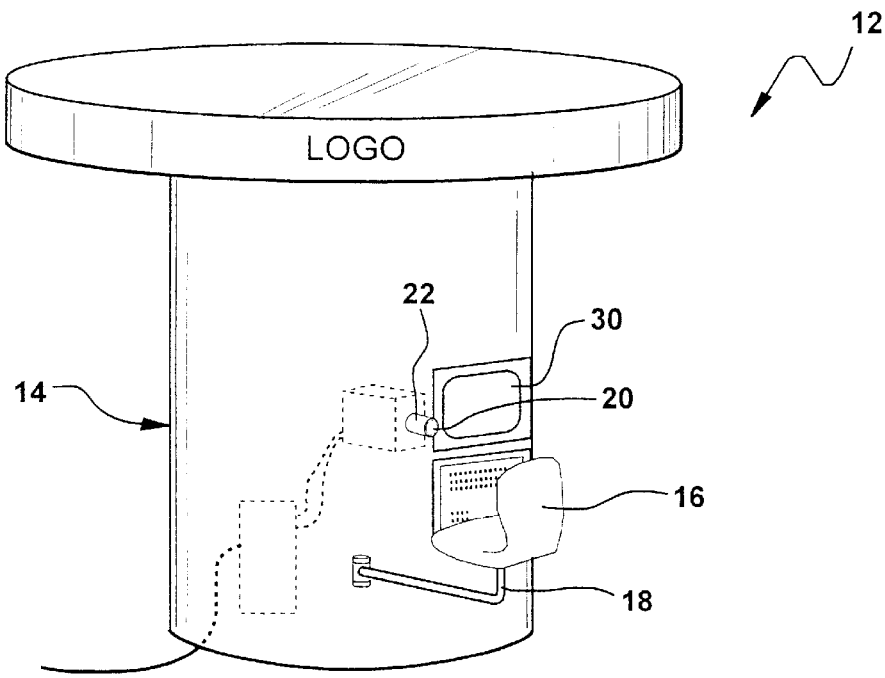
FIG. 2 is a pictorial representation of the internal components in the kiosk shown in FIG. 1.
Figure 3:
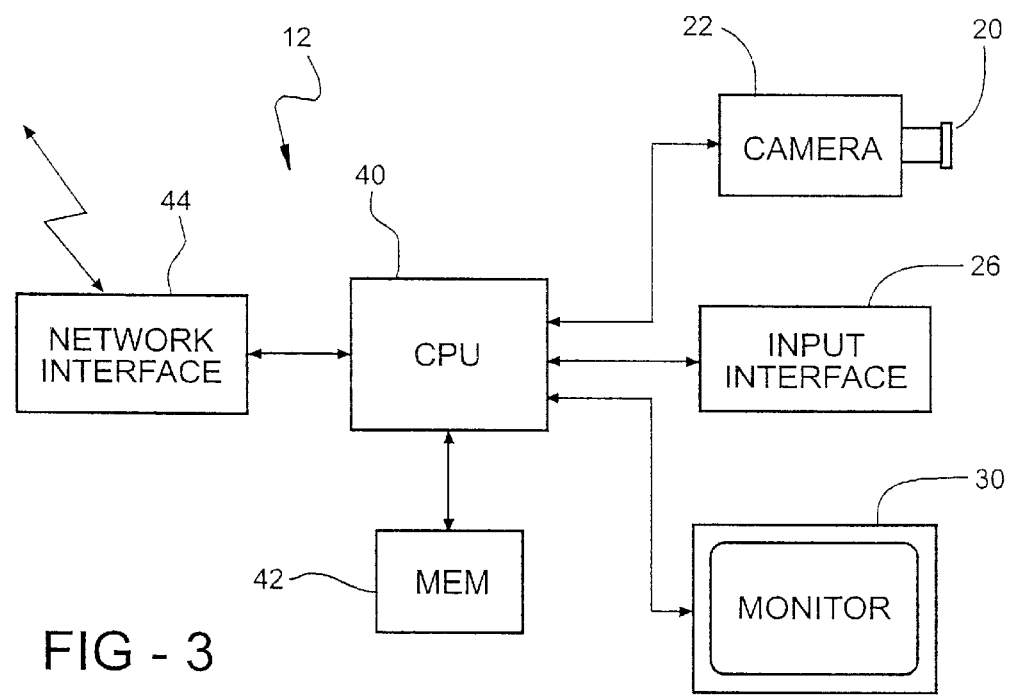
FIG. 3 is a block diagram of the internal components of a remote unit shown in FIG. 1.

Each remote unit 12 is in the form of a stand alone housing 14 which, in the exemplary embodiment shown in FIGS. 1 and 2, is in the form of a kiosk. The housing 14 may take any shape with the illustrative cylindrical shape being understood to be by example only. Square, and other multi-sided housing configurations are also possible.

The outer surfaces of the housing 14 are amenable to advertisements from local merchants as well as educational information concerning eye disease. Instructions for use of the retinal screening apparatus 12 may also be placed on the exterior of the housing 14.

As shown in FIGS. 1 and 2, a chair or seat 16 is optionally attached to the housing 14 by means of a support bracket 18.

The entire seat 16 and support bracket 18 may be fixedly or, preferably, pivotally attached to the housing 14. This enables the seat 16 to be pivoted into close proximity with the housing 14 so as not to protrude a great distance beyond the peripheral extent of the housing 14 when not in use.

It should be noted that the size of the seat 16 and the length of the bracket 18 may be selected to provide an appropriate focal distance for a patient from a fixation target 21 which is mounted in front of or slightly adjacent to a lens 20 of a camera 22 mounted within the housing 14. The lens 20 is covered by a protective plate, such as a transparent glass or plastic panel mounted in the side wall of the housing 14.

In certain applications, it may be desirable to dispense with the seat 16 and merely provide a mark on the floor at a set distance from the fixation target 21 to properly locate a patient for the retinal screening exam as described hereafter.

As shown in FIG. 1, a user interface 26 is mounted in the housing 14 with an exterior surface accessible through the wall of the housing 14. The input interface 26 may take a number of different forms, including a conventional keypad, pushbuttons or, as shown in FIGS. 1 and 2, a touchscreen.

The touchscreen 26 is usable to provide instructions to the user as well as to accept inputs by means of the user touching selected portions of the touchscreen 26 on which appear input selections, including a keyboard display to enable a user to enter user demographics, such as name, address, phone number, age, weight, sex, and other information pertinent to a retinal exam.

An optional display 30 in the form of a video monitor is also mounted in the housing 14. The monitor 30 is used, as described hereafter, to display clinical retinal photographs of different eye diseases as well as photographs of healthy eyes to enable a user to self compare their retinal image with a set of control retinal images. The monitor 30 can thus display both the patient's own retinal image as well as one control image of a diseased eye or a healthy eye.

It should also be noted that the user interface 26 when implemented in the form of a touchscreen may also be combined with the monitor 30 into a single touchscreen monitor as is readily available in the marketplace.

Preferably, the monitor 30 is a color monitor to more adequately display the retinal image.

Although not shown, a service door is provided in the wall of the housing 14 to allow access to the interior of the housing 14 for service or replacement of the various components of the retinal screening apparatus mounted within the housing 14.

The camera 22 is preferably a digital retinal camera that takes digital retinal photographs through a non-dilated pupil of a user seated in the chair 16 or standing at a spaced distance from the fixation target 21. By example, a digital retinal camera sold by Canon as model CR-5 camera using MVC 5000 retinal imaging software can be used to capture, display and store high resolution retinal images of patient conditions.

The camera 22 is preferably provided with an auto focusing lens system, including infrared sensors and a motor lens focusing drive to auto focus on a patient's eye. Alternately, a fixed focal length lens can be used.

For added clarity, a chin support may be mounted by means of a bracket, not shown, on the housing 14 so as to receive a patient's chin and position the patient's eyes at a set distance from the fixation target 21 and the adjacent camera 22.

Also housed with the housing 14 is a central processing unit 40, such as a microprocessor, microcontroller, etc. The central processor, hereafter referred to as a CPU 40, accesses a stored program contained in a memory 42, either contained within the microprocessor 40 or as a separate memory element connected in data communication with the CPU 40.

The CPU 40 thus is capable of generating instructions for use of the retinal screening apparatus 12 as well as receiving patient input demographics, displaying a set of control digital retinal images and patient retinal images on the monitor 30.

In use, the touchscreen 26 or, in a printed chart mounted on the housing 14 of the retinal screening apparatus 12, a set of instructions will be provided. A patient will input various patient demographics, such as name, address, telephone number, age, weight, sex, name and address of the patient's eye doctor, etc., into the CPU 40 via the touchscreen 26 or other input interface provided on the housing 14. A patient will sit in the chair 16 and fix his or her chin on the chin pad, if a chin pad is provided, or fix his or her forehead against a forehead rest, if provided. At a set time or by means of a start button provided on the housing 14, the apparatus 12 is activated. The camera 22 auto focuses the lens 20 to the proper focal length and takes a digital retinal image of one of the patient's eyes. The patient then shifts his or her position relative to the fixation target 21 and then repeats the above process to enable the camera 22 to take a digital retinal image of the patient's other eye.

The camera 22 outputs the digital images to the CPU 40 which converts the digital information into digital images which can be displayed on the monitor 30, either by themselves or in a side-by-side comparison with a set of control images showing healthy and diseased eyes.

Figure 4:
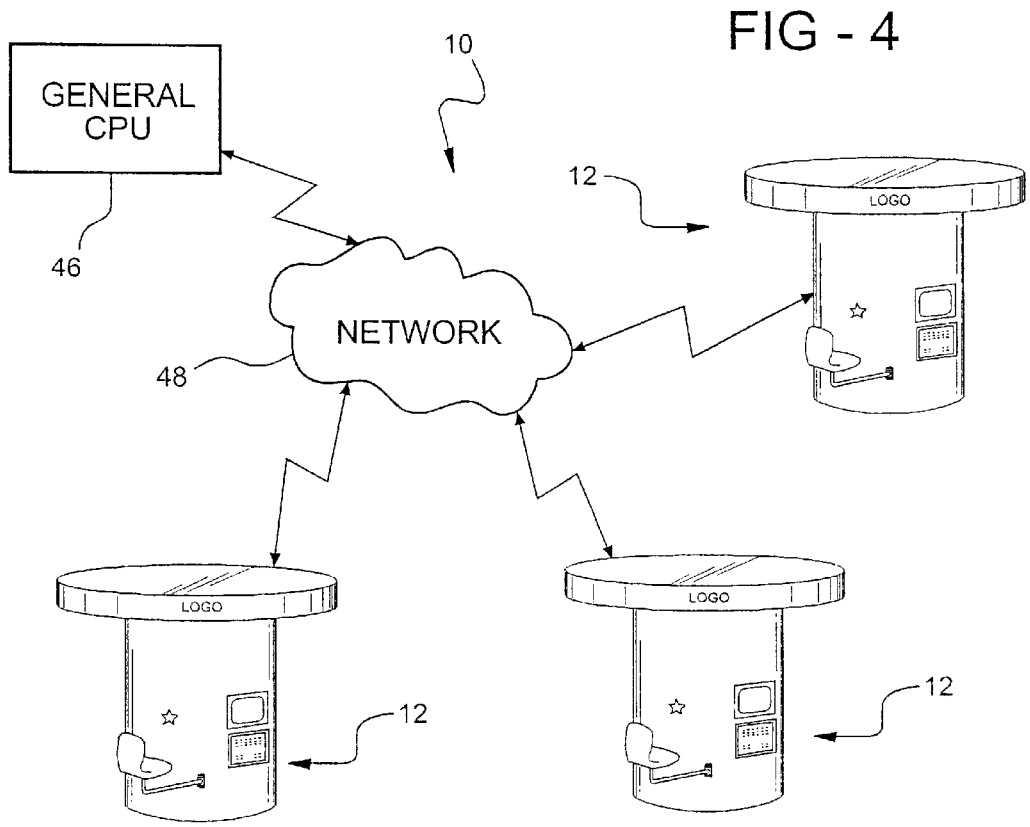
FIG. 4 is a pictorial representation of a wide area implementation of the retinal screening apparatus of the present invention.

An important feature of the present apparatus 10 is a network connection provided by a network interface 44 from the CPU 40 to a central CPU or station 46 shown in FIG. 4. The network interface 44 provides connection to a data communication network 48, also shown in FIG. 4. The data communication network 48 may be any type of data communication network, such as a wide area or local area telephone network using dedicated telephone lines through a modem which comprises the network interface 44 to the central station 46 or, if the patient can input his or her eye doctor's address and telephone number, directly to his or her eye care physician.

The network 48 may also comprise wireless data communication networks, such as the Internet. In this instance, the network interface comprises a conventional modem connection to a service provider. The central station 46 will have an IP address allowing access to the data transmitted from any of the remote units 12. Alternately, cellular telephone and satellite systems, etc., may constitute the network 48.

Likewise, if a patient can input his or her eye doctor's Internet address or e-mail address, the digital retinal images can be sent directly through the Internet 48 to the specified eye doctor.

In the case where the digital retinal information is sent to the central station 46, the central station 46 can print the digital retinal images for examination by an ophthalmologist or eye care specialist. The diagnosis of any eye disease can be handled with different levels of concern and educational information sent back to the patient. When severe eye disease is detected, a higher degree of concern will be raised in follow-up with the patient advising the patient to contact an eye care specialist would then be strongly recommended by either by telephone call, letter or both. If the patient's eye doctor is provided by the patient, the same information can be sent directly to the specified doctor.

The end result of the use of the retinal image apparatus of the present invention is that more people are exposed to easy and free retinal eye examinations thereby increasing the probability of identifying patients with diabetic retinopathy, glaucoma or other eye diseases earlier in the course of the disease. As numerous studies have shown, early intervention with medical treatment can significantly reduce the risk of loss of vision and blindness.

In general, the retinal examination apparatus of the present invention includes a housing, an auto focus, digital retinal camera mounted within the housing, the user interface for inputting patient demographics, a display for displaying captured digital retinal images of the patient's eyes and/or comparing the patient's digital retinal images with healthy and diseased eyes for self comparison by the patient, and a network interface for connection to a communication network wherein the captured digital retinal images of each patient are transmitted to the patient's doctor or to a central station for comparison and follow-up, if follow-up is needed.

Although the present invention has been described as a retinal screen apparatus devised specifically for taking and transmitting digital retinal images of a patient's eyes, the present invention also contemplates the retinal screening process as being but one of a number of separate and/or available functions which may be provided in a so-called "medical kiosk". In this configuration, a housing similar to the housing 14 may also incorporate other medical test equipment, such as glucose test equipment utilizing an oxygen sensor attachable to a patient to measure the patent's blood sugar levels. A blood pressure cuff may also be provided to obtain a patient's blood pressure. Pulmonary function equipment including a breathing tube and suitable test equipment may also be mounted within the housing 14 to measure a patient's pulmonary capacity. Of course, each specific test would require its own test equipment mounted within the housing 14 to measure and digitize the input data collected during each specific test. However, the resulting data, when properly formatted by the CPU 40, can then be transmitted via the network 48 to the central station 46. The central station 46 will then compare each specific test data with specific body functions standards, such as safe or unhealthy glucose levels, blood pressure levels or pulmonary functions. Appropriate results will then be transmitted to the patient's doctor or primary health care provider as indicated on the input demographic information or sent directly to the patient with an explanation and whether or not further physician examination is appropriate.

What is claimed is:

1. A medical screening apparatus for executing a medical test on a patient comprising:
    an integrated housing having components for fully automated testing initiated in response to patient activation;
    a user interface mounted in the integrated housing for inputting user related data;
    a medical test apparatus mounted in the integrated housing for automatically executing a medical test on a user and generating a test output;
    means communicating with the medical test apparatus, for transmitting the test output and patient demographics to a remote analysis site.

2. The medical screening apparatus of claim 1 further comprising:
    automated control means, mounted in the integrated housing, for controlling the user interface, the activation of the medical test apparatus and the operation of the transmitting means.

3. The medical screening apparatus of claim 2 wherein:
    the control means includes a central processing unit executing a control program stored in a memory coupled to the central processing unit.

4. The medical screening apparatus of claim 1 wherein the transmitting means comprises:
    means for communicating the test output via a global telecommunication network.

5. The medical screening apparatus of claim 1 wherein the user interface comprises:
    a video display terminal mounted in the integrated housing.

6. The medical screen apparatus of claim 5 wherein:
    the video display terminal is at least one of a user interface and a video output display of the test output.

7. The medical screening apparatus of claim 5 wherein:
    the video display terminal is a user interface and a video output display for displaying the test output to the user.

8. The medical screening apparatus of claim 1 wherein:
    the medical test apparatus is a retinal screening apparatus.

9. The medical screening apparatus of claim 8 wherein:
    the retinal screening apparatus includes a digital retinal camera.

10. The medical screening apparatus of claim 8 further comprising:
    means for establishing a predetermined position of the user's eye with respect to the medical test apparatus in the integrated housing.

11. The medical screening apparatus of claim 10 wherein the position establishing means comprises:
    a chin support mounted at a fixed distance from the integrated housing.

12. The medical screening apparatus of claim 10 wherein the position establishing means comprises:
    a seat mounted on the housing at a fixed distance from the integrated housing.

13. A method for executing a medical test on a user patient, the method comprising the steps of:
    initiating a fully automated medical test in response to patient activation of a testing apparatus included in an integrated housing;
    providing a user interface in the integrated housing for receiving user data;
    providing a medical test apparatus in the integrated housing for executing a medical test on a patient and generating a test output; and
    transmitting the test output to a remote site for analysis.

14. The method of claim 13 wherein the transmitting step further comprises:
    transmitting the test output and the user data to the remote site via a global telecommunication network.

15. The method of claim 13 wherein the step of providing the user interface comprises the steps of:
    providing a user interface for inputting user data in a video output terminal for displaying the test output.

16. The method of claim 13 wherein the medical test apparatus executes a retinal screening test.

17. The method of claim 16 wherein the step of providing a medical test apparatus includes providing a digital retinal camera in the integrated housing.

18. The method of claim 16 further comprising a step of:
    establishing a predetermined position of the user's eye with respect to the medical test apparatus in the integrated housing.

* * * * *